United States Patent [19]

Ferenczi et al.

[11] Patent Number: 4,995,939
[45] Date of Patent: Feb. 26, 1991

[54] METHOD AND APPARATUS FOR DETERMINING THE LAYER THICKNESS OF SEMICONDUCTOR LAYER STRUCTURES

[75] Inventors: György Ferenczi; Katalin Erdélyi; Mária Somogyi; János Boda, all of Budapest; György Füle, Pecel; Gábor Aszódi, Budapest, all of Hungary

[73] Assignee: Magyar Tudomanyos Akademia Muszaki Fizikai Kutato Intezete, Hungary

[21] Appl. No.: 301,889
[22] PCT Filed: May 4, 1988
[86] PCT No.: PCT/HU88/00030
    § 371 Date: Feb. 8, 1989
    § 102(e) Date: Feb. 8, 1989
[87] PCT Pub. No.: WO88/09053
    PCT Pub. Date: Nov. 17, 1988

[30] Foreign Application Priority Data

May 4, 1987 [HU] Hungary ............................ 1989/87

[51] Int. Cl.⁵ ............................................. G01N 27/46
[52] U.S. Cl. ..................................... 156/627; 156/345; 204/1 T; 204/129.2; 204/129.3; 204/129.25; 427/9; 427/10; 324/439; 324/444
[58] Field of Search ....................... 156/627, 626, 345; 204/129.2, 129.3, 1 T; 427/9, 10; 324/439, 444

[56] References Cited

U.S. PATENT DOCUMENTS

| | | | |
|---|---|---|---|
| 3,874,959 | 4/1975 | Hoekstra et al. | 156/345 X |
| 3,902,979 | 9/1975 | Thomas | 204/129.3 |
| 4,028,207 | 6/1977 | Faktor et al. | 204/129.3 |
| 4,310,389 | 1/1982 | Harbulak | 204/129.2 X |
| 4,487,661 | 12/1984 | Barraud et al. | 204/400 X |

OTHER PUBLICATIONS

Characterization of Semiconductor Materials and Structures . . . (Current Topics in Materials Science, vol. 6, 1980), M. M. Factor et al.
Capacitance-Voltage Profiling and the Characterisation of III-V Semiconductors . . . (Semicond. Sci. Technol. 1, pp. 7-27, 1986), P. Blood.
Admittance Spectroscopy of Impurity Levels in Shottky Barriers (J. Appl. Phys. 46, pp. 2204-2214, 1975), D. L. Losee.

Primary Examiner—David Simmons
Assistant Examiner—Thi Dang
Attorney, Agent, or Firm—Handal & Morofsky

[57] ABSTRACT

In a process for determining the layer thickness of semiconductor layer structures, a sample of a multilayer semi-conductor (4) is placed in contact with an electrolyte (2) then subjected to anodic etching during which the depth of etching is determined by integration of the current. During etching, the sample (4) is also excited by an electric signal and the real component of the admittance and hence the conductance of the probe at the frequency of excitation is determined, the extreme values of this component are analyzed, and the values of the depth of etching corresponding to these extremes, which characterize the junctions between the layers of the sample (4) tested, are determined. The installation for implementing the procedure contains a cell (1) filled with electrolyte (2) in which is immersed a graphite electrode (5), a saturated calomel electrode (6), and a platinum electrode (7) surrounding the surface of the sample (4) subjected to etching, electrodes (8,9) neither of which touch the surface of the sample (4) subjected to etching, a potentiostat (13) which is connected to the calomel electrode (6) and the direct current source (12), the current integrator (14), which receives the etching current intensity signal, a generator (15) which emits a periodic signal between the sample (14) and the metal electrode, and the measurement element (16) for measuring the conductance of the sample (4).

13 Claims, 2 Drawing Sheets

METHOD AND APPARATUS FOR DETERMINING THE LAYER THICKNESS OF SEMICONDUCTOR LAYER STRUCTURES

The invention relates to a method and apparatus for determining the layer thickness of semiconductor layer structures, i.e., the layer thickness of each layer of a multilayer semiconductor structure, primarily of hetero transitions.

When III-V type semiconductors are used for opto electronic applications or in the field of microelectronics when such semiconductors are used as fast operating switching elements, layer structures are widely used which consist of thin layers of differing materials wherein the layer thickness may vary between 5 nm and 1–2 μm. In case of so-called super grid structures the number of layers can be as high as 60–100. When electron microscope is used for the examination or determination of such a high number of layers with such a small thickness, the accuracy will not be sufficiently high and the determination will be limited to the location of the metallurgic transition and it will not be effective for measuring the physical transition. Conventional C-V measurements using a metal contact cannot provide sufficient accuracy either, because owing to the typically high ($10^{17}$ atoms/cm$^3$) concentration of charge carries the depth of the attainable depletion zone is below 1 μm and the layer structure which should be examined can have a thickness of several times 10 μm.

The most advanced known technique for the determination of the layer thickness utilizes profile-measurement methods based on C-V measurements of electrolyte-semiconductor transitions. Such a method is disclosed in the papers of M. M. Faktor, T. Ambridge, C. R. Elliott and J. C. Regnault: 'The Characterization of Semiconductor Materials and Structures Using Electrochemical Techniques' (Current Topics in Materials Science, Vol. 6 1980, Ed: E. Kaldis, North-Holland, Amsterdam), as well as in the paper of P. Blood: 'Capacitance-Voltage profiling and the Characterization of III-V Semiconductors Using Electrolyte Barrier' (Semicond. Sci. Technol. 1, pp. 7–17, 1986).

In this method an electrolyte was used which, on the one hand was capable of ensuring that a depletion zone be established between the electrolyte and the semiconductor with a suitable bias and on the other hand was able to ensure that the electrolyte can penetrate till any required depth in the examined sample by means of anodic etching. The depletion zone was established by using a typically 1 V reverse bias, the capacitance of the sample was measured by means of a modulating signal having a typical frequency of 3 kHz derived by a frequency of about 30 Hz and this value was used for the determination of the concentration of the examined semiconductor sample. If the current flowing through the electrolyte is integrated, then the depth of penetration of the etching front can be determined by using Faraday's law.

This method provides good results when thicker layers are examined, in case of thinner layers, however, very small etching currents should be adjusted, therefore the etching process goes on in very small steps, i.e. steps of 1 nm only, because otherwise an integrated layer would be obtained instead of the layers to be examined (see FIG. 23 of the above referred publication of 'Blood'). From these limitations it follows that the examination requires long time and the results of the measurements can be dependent from fluctuations of the temperature, and for the determination of the actual location of the transition from the results of the measurements only approximative calculations exist which have errors as high as the layer-thickness.

It is known from the literature of the pertinent art that in the presence of deep levels the realistic member of the admittance follows the high frequency measuring signal with a phase-delay, if the frequency of the measuring signal is higher than the time constant of the thermic emission of the deep levels. This fact is supported by references, e.g. in the publication of D. L. Losee: 'Admittance Spectroscopy of Impurity Levels in Schottky Barriers' (J. Appl. Phys. 46. pp. 2204–2214, 1975).

It is also a known fact that on the boundary surface of semiconductor layers of differing compositions, such as GaAs and GaAlAs, boundary surface states are formed due to energy band discontinuities obtained by the differing widths of forbidden gaps, and such boundary surface states are bound in the full width of the forbidden gap.

The object of the invention is to provide a method for determining the layer thickness of multilayer semiconductor structures which is based on a novel principle of measurement that enables the faster and more accurate determination of the thickness of the respective layers even in case if a large number of thin layers is examined. A further object of the invention is to provide an apparatus for carrying out the method.

For getting to the discovery on which the present invention is based we started from the fact that according to the above referred publication of D. L. Losee a maximum is obtained in the conductance signal as a function of the frequency of the high-frequency measuring signal, if $$\omega\tau = 1 \tag{1}$$

in which $\omega$ designates the frequency of the measuring signal and $\tau$ designates the time constant of the thermal emission of the deep level.

If the high-frequency conductance is measured at a fixed frequency (e.g. between 3 and 10 kHz) then states will always be found for which the equation (1) is true i.e. if by the progression of the etching front the depletion zone reaches the boundary surface of two layers, then an extreme value is obtained in the conductance signal. This recognition forms the basic idea of the present invention.

Since the built in field is also capable of providing the depletion zone, there is no need for providing a separate reverse bias either.

When the method according to the invention is carried out, two examinations are made directed to simultaneously occurring events:

(a) the examined multi-layered semiconductor chip is anodically etched by means of direct current electrolysis as a function of time, in which the thickness of the removed layer is measured;

(b) simultaneously with the anodic etching process the real and imaginary components of the admittance of the semi-conductor-to-electrolyte boundary surface are measured as a function of the depth of the etching which latter one can be determined from the time-current-thickness data of the measurements (a). The locations of the boundary surfaces of layers with differing material compositions and/or doping will be at the extreme values of the conductance signal (which is the real component of the admittance) i.e. such extreme values determine such locations.

According to the invention a method has been provided for determining the layer thickness of the respective layers of a multilayer semiconductor structure, in which a sample of the structure is examined, the sample is contacted with an electrolyte and it is etched anodically, during the etching process the actual depth of the etching is determined by means of the integration of the etching current, the sample is excited by an electrical signal while it is being etched and the response to this signal is measured, and according to the invention on the frequency of the exciting signal the real component i.e. the conductance of the admittance value of the sample is measured, the extreme values of this component are examined and the etching depth data associated with such extreme values are recorded which define the transitions of the examined layers of the sample.

When n-type sample is measured, then the surface of the sample is excited by means of light which is in contact with the electrolyte.

The time required for completing the method can be shortened substantially if the etching step is carried out continuously during the performance of the whole method.

By the appropriate adjustment of the parameters of the method it can be ensured that the whole surface of the sample be evenly etched.

It is preferable for the measurement if the excitation is carried out by a sine signal having a frequency between 500 Hz and 10 kHz.

From the point of view of the method it is preferable if the etching is made by a current between 1 $\mu$A and 100 $\mu$A.

It is also preferable if the exciting signal is coupled between a platinum electrode immersed in the electrolyte and surrounding the etched surface of the sample and at least two electrodes with sharp-pointed ends pressed to a surface of the sample other than said etched surface.

The contact to the sample can be improved if an electric discharge is provided between the sharp-pointed electrodes and the sample before the actual measurement is started, whereby the material of the sharp end of the electrode is slightly mixed in the sample.

According to the invention an apparatus has also been provided for carrying out the method which comprises a cell filled with an electrolyte, a carbon electrode immersed in the electrolyte, a saturated calomel electrode and a platinum electrode surrounding the etched surface of the sample, electrodes contacting surfaces of the sample not exposed to the etching, a potentiostat coupling an adjustable potential between the carbon electrode and the sample, the potentiostat is connected to the calomel electrode and to a direct current source, a current integrator receiving a signal representing the etching current, a generator coupling a periodical signal between the metal electrode and the sample, and a unit measuring the response of the sample to the periodical excitation, and according to the invention said measuring unit is a conductance measurement unit.

The conductance measuring unit comprises preferably a lock-in amplifier and a phase-sensitive amplifier.

It is preferable if the output of the conductance measuring unit is connected to first input of a signal processing unit which latter has a second input coupled to output of the current integrator.

The signal processing unit comprises preferably a plotter capable of drafting an etching depth versus conductance diagram.

The most significant advantage of the technical solution according to the invention lies in the increased accuracy of measurement and in the substantial reduction of time required for carrying of the measurements. The continuous etching process results namely substantially shorter measuring time compared to known methods, in which the etching process had to be stopped at each layer. The accuracy of the measurement is increased and the associated calculations are simplified by means of the fact that the maximum of the conductance lies always at the locus of the physical transition zone.

The invention will now be described in connection with preferable embodiments thereof, in which reference will be made to the accompanying drawings. In the drawing:

DETAILED DESCRIPTION OF THE DRAWINGS

Figure 1:
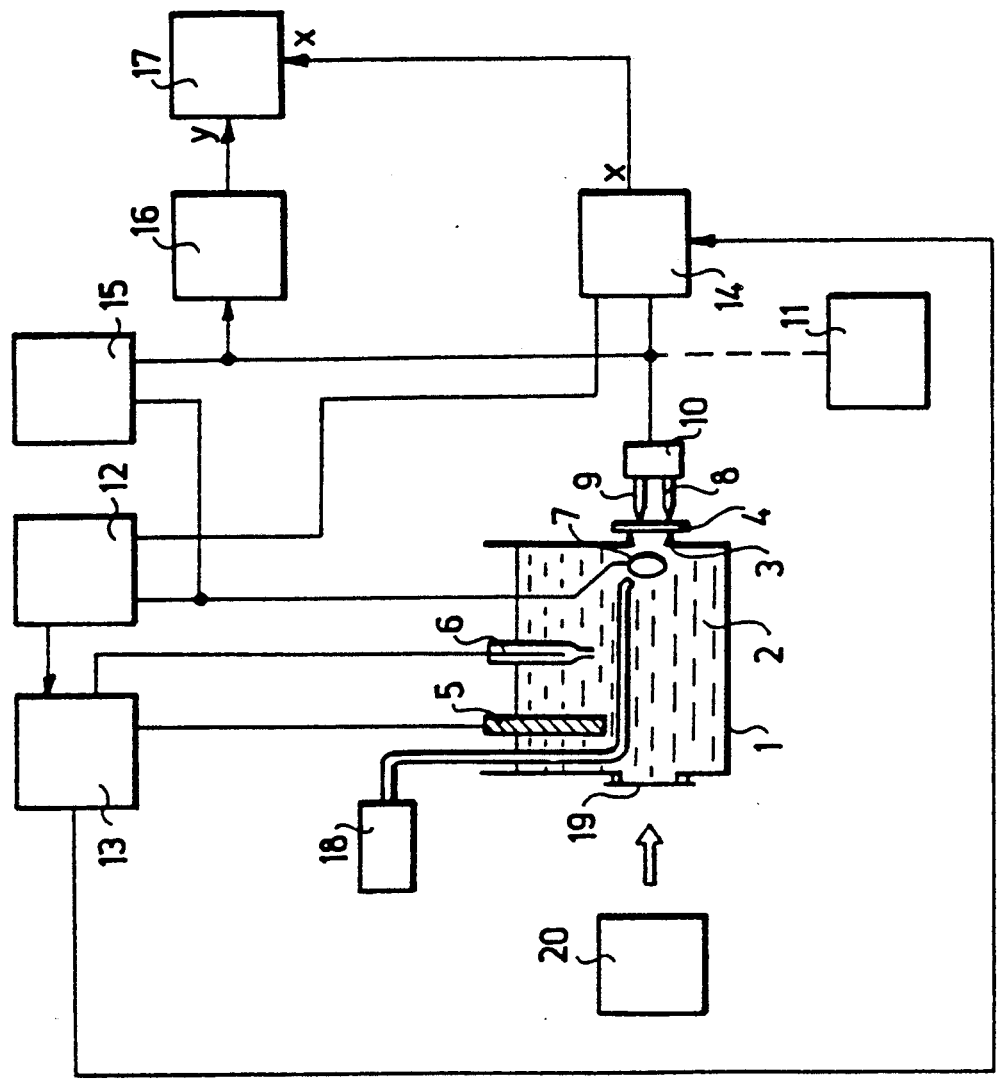
FIG. 1 shows the simplified block diagram of the apparatus according to the invention.

In the arrangement scheme of FIG. 1 the internal structure of a conventional cell 1 is shown which contains an electrolyte 2 which, in the exemplary embodiment, is formed by a 0.1m-2m KOH solution. According to experimental results this electrolyte provides the most favorable conditions for the measurements, however, satisfactory results are obtained if other electrolytes i.e. NaOH, HCl or Tiron ® are used which have similar concentration. At a side of the cell 1 an aperture is formed which has edges provided with seal 3. The aperture is closed by sample 4 made of the semiconductor to be examined pressed to the seal by means of a resilient bias.

Electrodes required for the measurements are immersed in the electrolyte 2 in the cell 1, and they comprise carbon electrode 5, saturated calomel electrode 6 provided a reference voltage and a ring shaped platinum electrode 7 surrounding the aperture in front of the sample 4. The performance of the measurement requires the establishment of an ohmical contact to the rear and/or frontal surface of the semiconductor sample 4. Such a contact can be implemented by means of tungsten electrodes 8, 9 having sharp tips curved typically with a radius of 25 $\mu$m.

For the sake of providing a proper and controllable contact the application of a plurality i.e. at least two platinum electrodes is required which are pressed resiliently to the sample 4 by means of biasing member 10. It is preferable if the sharp ends of the electrodes 8, 9 are coated by a contact metal (i.e. by Sn or In) corresponding to the material of the sample 4. The quality of the contact can further by improved if before starting the measurements a suitably charged capacitor is discharged between the semiconductor and the electrodes 8, 9 by means of a burning-in unit 11 which results in that a small amount of metal will be alloyed in the material.

Electronic units of the measuring arrangement comprise direct current source 12 provided the required direct current voltage, potentiostat 13 coupled to the calomel electrode 6, carbon electrode 5 and to the direct current source 12, a current integrator 14 coupled to the potentiostat 13 and to the electrodes 8, 9, a generator 15 exciting the sample 4 with a high frequency signal, a conductance measuring unit 16 measuring the real component of the admittance of the sample 4 and a signal processing unit 17 receiving output signals of the conductance measuring unit 16 and of the current integrator 14.

The arrangement comprises pump 18 which, for providing a uniform etched surface, causes the electrolyte 2 to continuously circulate or mixes the electrolyte by bubbling $N_2$ gas therethrough to remove thereby the etched material from the surface of the semiconductor.

The cell 1 comprises window 19 opposite to the sample-receiving aperture through which the sample 4 can be illustrated by light source 20.

During the measurement the surface of the sample 4 which is in contact with the electrolyte 2 is anodically etched by means of a direct current voltage established between the carbon electrode 5 and the electrodes 8, 9. The direct voltage required to the anodical measurement (i.e. the etching voltage) is chosen on the basis of the I-V characteristic curve of the semiconductor sample 4. The potentiostat 13 is used for the voltage adjustment, and in this adjustment the voltage supplied by the calomel electrode 6 is used as a reference value. The potential formed spontaneously between the solution i.e. the electrolyte 2 and the surface of the semiconductor sample 4 will be referred to as the rest potential of the solution and its value is interpreted with respect to the calomel electrode 6.

For carrying out the measurement there are certain conditions which should be kept. These are:
  (1) Independent from its type of conductance the voltage of the semiconductor should be positive relative to the carbon electrode 5 in order that anodic etching process can take place.
  (2) In case of an n-type material the etching will take place if the semiconductor is illuminated by a light which has an energy higher or equal to the forbidden band of the semiconductor, whereby the minority charge carriers (holes) required for the etching process are created.
  (3) An electrolyte 2 should be chosen, which ensures that:
    the anodically oxidized product remain solved state,
    during the etching process the surface inhomogeneity of the semiconductor sample be as small as possible.

The conditions imposed on the electrolyte 2 can be met by the examplary solutions defined in the present specification.

In addition to the selection of the appropriate type of electrolyte the uniform surface (i.e. which has a minimum roughness) can be ensured by the adjustment of the following parameters:
(a) In case of a p-type material an etching current of 1 $\mu$A to 100 $\mu$A is adjusted by using an appropriate etching voltage. Since the etching voltage causes a forward bias in the semiconductor sample 4, the conductance measurement requires that a suitable reverse bias be established by means of the direct current source 12 between the platinum electrode 7 and the electrodes 8, 9. This bias is typically 0.2–0.6 V with respect to the calomel electrode 6.
(b) In case of an n-type material the etching current of 1 $\mu$A to 100 $\mu$A is adjusted by the appropriate selection of the light intensity of the light source 20 and of the etching voltage.
(c) In both cases the etching products should be removed by the stirring of the electrolyte. As already referred to hereinabove, this is the purpose of using the pump 18.

For performing the high frequency admittance (or impedance) measurement the generator 15 is used to supply a sine wave signal with low distorsion between the platinum electrode 7 and the electrodes 8, 9 which form the ohmical contact of the semiconductor sample 4, and the repetition frequency of this signal can be varied between 500 Hz and 10 kHz and its effective voltage is between 5 mV and 50 mV. The response of the semiconductor sample (which is a current signal with a phase shifted relative to the voltage) is coupled to the conductance measuring unit 16 comprising a double lock-in amplifier and a phase-sensitive rectifier, and the real and imaginary components (i.e. the conductance and susceptance) of the admittance or, if required, the two components of the impedance are supplied separately at the output of the unit 16.

The etching current of the anodic etching process is received and processed by the current integrator 14 and it supplies layer thickness output data evaluated in accordance with the geometric size and density of the sample under test.

The signal processing unit 17 receives the output admittance signal of the conductance measuring unit 16 as a y component and the layer thickness value determined by the current integrator 14 as an x component and displays the x-y function. If the signal processing unit 17 is implemented by a computer, then respective analog-go-digital converters are used for coupling the computer input with said analog outputs. As a result of the measurement the conductance value is obtained as a function of the etching depth (which is the thickness of the removed layer or layers), and the distances between the extreme values of this function give the thicknesses of the respective layers.

EXAMPLE

The semiconductor sample 4 under test was formed by a ten-layer structure made on an n-type GaAs substrate which comprised five n-type $Ga_{0.6}Al_{0.4}As$ layers and five n-type GaAs layers arranged in alternating order. The covering layer was a 0.5 $\mu$m thick GaAs layer, and the thickness of the other layers was 0.1 $\mu$m. The electrolyte 2 was a 1n KOH solution. The sample 4 was illuminated by the light source 20 which comprised a halogen bulb, an appropriate focusing arrangement and an infrared filter cutting off the range of wavelengths above 1.3 $\mu$m.

The measurement was carried out at room temperature i.e. at 25° C.

The rest potential measured without illumination was −0.8V with respect to the saturated calomel electrode 6.

The etching voltage used for the etching process was $V_{etch} = +0.2V$ which tried to decrease the rest potential.

The etching current varied between $I_{DC}$: 5 and 10 $\mu$A.

During the measurement the etching was performed continuously and the measurement took 180 minutes.

Figure 2:
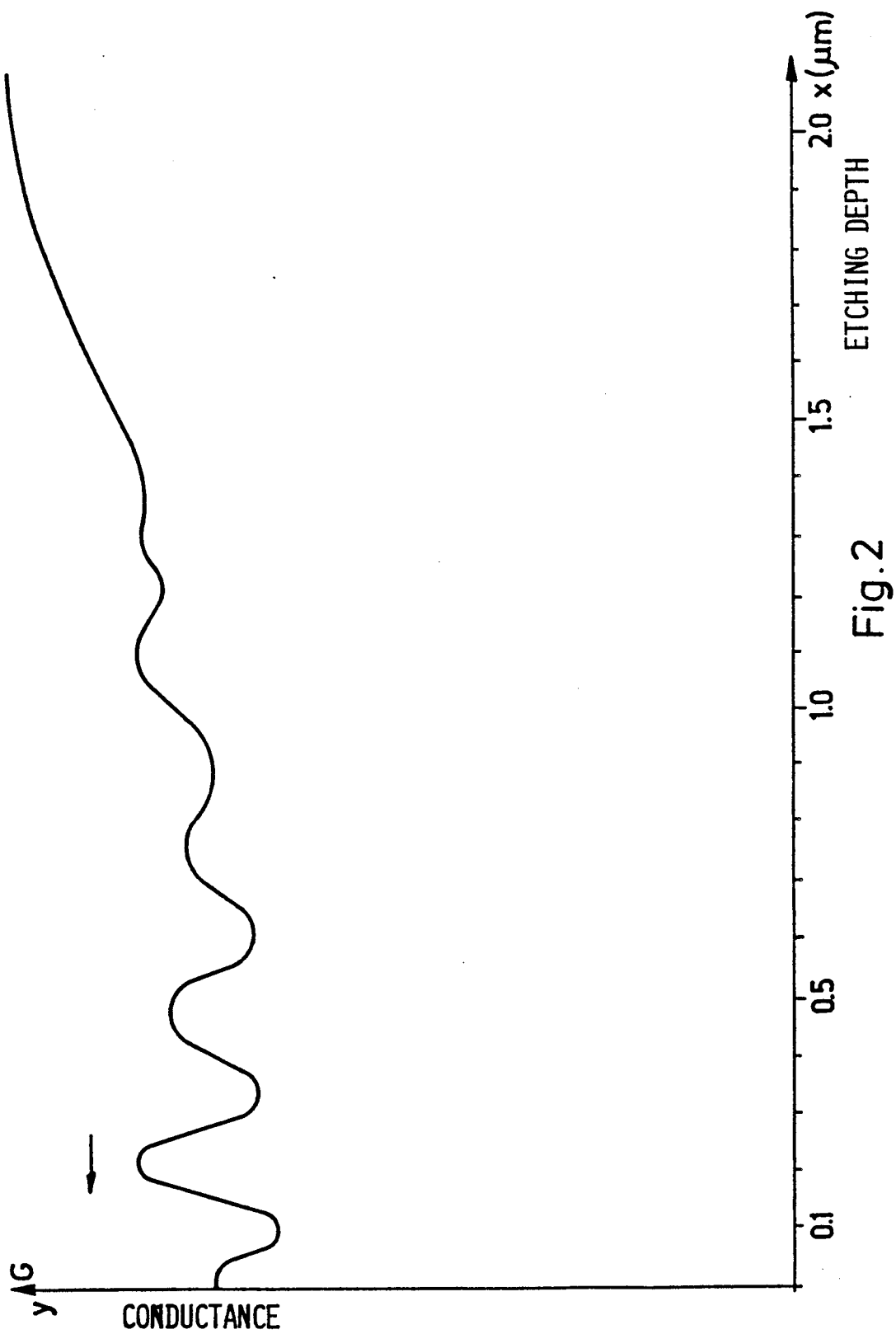
FIG. 2 is a diagram showing the results of an exemplary measurement.

The result of the measurement is illustrated on the conductance-etching depth curve of FIG. 2. The thickness of the overall ten layers can well be read from the diagram. The locations of the boundary transition zones appear as the extreme values, maximums or minimums of the conductance signal depending on whether the energy of the forbidden band decreases or increases at the particular boundary surface.

It should be noted that the energy relating to GaAs is about $E_G=1.4$ eV and the energy relating to $Ga_{0.6}Al_{0.4}As$ is about $E_G=1.8$ eV.

From the example it can well be seen that owing to the continuous etching the time of measurement has been reduced substantially compared to earlier measurement methods and the result obtained was sufficiently accurate.

We claim:

1. A method for determining the layer thickness of semiconductor layer structures, in which a multilayer semiconductor sample is examined, comprising the steps of contacting a surface of said sample with an electrolyte, anodically etching said surface using an etching current, determining, during the etching process, the actual etching depth, by integrating said etching current, said sample being excited by a periodic electrical signal while said sample is being etched and measuring a response to said periodic signal in a manner such that at the frequency of the exciting signal a real component, comprising the conductance of the admittance, of the sample is measured, wherein the extreme values of said component are examined and the etching depth data associated with said extreme values are recorded, said extreme values defining the transitions of the examined layers of the sample.

2. A method as claimed in claim 1, wherein said sample is an n-type sample and said periodic electric signal is produced by means of light.

3. A method as claimed in claim 1, wherein said etching process is carried out continuously during the whole measurement.

4. A method as claimed in claim 1, wherein said surface of the sample is uniformly etched.

5. A method as claimed in claim 1, wherein said periodic electric signal is a sine signal having a frequency between 500 Hz and 10 kHz.

6. A method as claimed in claim 1, wherein said etching process is carried out by a current between 1 $\mu A$ and 100 $\mu A$.

7. A method as claimed in claim 1, wherein said exciting signal is coupled between a platinum electrode immersed in said electrolyte and at least two electrodes with sharp-pointed ends pressed to a surface of the sample other than said etched surface.

8. A method as claimed in claim 7, wherein before measurement is started, an electric discharge is provided between said sharp-pointed electrodes and said sample, whereby the material of the sharp end of said sharp-pointed electrodes is slightly alloyed in said sample.

9. An apparatus for determining layer thickness of a multilayer semiconductor structure comprising a cell filled with an electrolyte, a carbon electrode immersed in said electrolyte, a saturated calomel electrode immersed in said electrolyte, a metal electrode also immersed in said electrolyte and being positioned so as to surround an etched surface of a sample to be etched, a pair of additional electrodes for contacting at least one surface of the sample not exposed to said electrolyte, said carbon electrode and said pair of additional electrodes cooperating so as to establish a direct current voltage for anodically etching the sample a potentiostat coupling an adjustable potential between said carbon electrode and said sample, the potentiostat being connected to said calomel electrode and to a direct current source, a current integrator for receiving a signal representing an etching current, a generator for exciting the sample with a periodical signal by coupling said periodical signal between said metal electrode and said sample and a unit measuring the response of said sample to the periodical excitation, wherein said measuring unit is a conductance measuring unit.

10. An apparatus as claimed in claim 9, wherein said conductance measuring unit comprises a lock-in amplifier and a phase-sensitive amplifier.

11. An apparatus as claimed in claim 9, wherein the output of said conductance measuring unit is connected to a first input of a signal processing unit that has a second input coupled to an output of said current integrator.

12. An apparatus as claimed in claim 11, wherein said signal processing unit comprises a plotter for drafting an etching depth versus conductance diagram.

13. An apparatus as claimed in claim 9, wherein said metal electrode comprises platinum.

* * * * *